US006380176B2

(12) United States Patent
Takahashi et al.

(10) Patent No.: US 6,380,176 B2
(45) Date of Patent: Apr. 30, 2002

(54) METHOD FOR INHIBITING NON-INTENTIONAL BEHAVIOR WITH A RUNNING NEURON INHIBITORY SUBSTANCE

(75) Inventors: Michio Takahashi; Makoto Bannai, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/816,396

(22) Filed: Mar. 26, 2001

(30) Foreign Application Priority Data

Mar. 28, 2000 (JP) ......................... 2000-088453

(51) Int. Cl.$^7$ ................ A61K 31/66; A61K 31/44; A61K 31/42; A61K 31/195; A61K 31/55
(52) U.S. Cl. ................ 514/114; 514/302; 514/354; 514/380; 514/567; 514/221
(58) Field of Search ................ 514/114, 302, 514/354, 380, 567, 221

(56) References Cited

PUBLICATIONS

J. Gerlach, et al., Psychopharmacology, vol. 56, pp. 145–151, "Effect of Baclofen on Tardive Dyskinesia," 1978.
S. M. Sainati, et al., Pharmacology, Biochemistry & Behavior, vol. 18, pp. 407–414, "Intra–Raphe Benzodiazepines Enhance Rat Locomotor Activity: Interactions with GABA," 1983.
I. Shoulson, et al., Annals of Neurology, vol. 4, No. 3, pp. 279–284, "Huntington's Disease: Treatment with Muscimol, A GABA–Mimetic Drug," Sep. 1978.
W. Froestl, et al., J. Med. Chem. vol. 38, No. 17, pp. 3297–3312, "Phosphinic Acid Analogues of GABA. 1. New Potent and Selective GABA$_B$ Agonists," 1995.
W. Howson, et al., Bioorganic & Medicinal Chemistry Letters, vol. 3, No. 4, pp. 515–518, "Biological Activity of 3–Aminopropyl (Methyl) Phosphinic Acid, A Potent and Selective GABA$_B$ Agonist with CNS Activity," 1993.

R. Mayeux, et al., Neurology, vol. 29, pp. 1616–1619, "Poriomania," Dec. 1979.
T. Yokawa, et al.; "The Ventromedial Nucleus of the Hypothalamus Outputs Long–Lasting Running in Rats"; Physiology & Behavior; vol. 46, 1989, pp. 713–717.
Takashi Yokawa, et al.; "Hyper–Running Activity Originating from the Hypothalamus is Blocked By GABA"; Physiology & Behavior, vol. 47, 1990, pp. 1261–1264.
Kazumi Narita, et al.; "Interaction Between Excitatory and Inhibitory Amino Acids in the Ventromedial Nucleus of the Hypothalamus in Inducing Hyper–Running"; Brain Research, 603, 1993, pp. 243–247.
Kazumi Narita, et al.; "Concomitant Regulation of Running Activity and Metabolic Change by the Ventromedial Nucleus of the Hypothalamus"; Brain Research, 642, 1994, pp. 290–296.
K. Narita, et al.; "Efferent Pathways Involved in the Running Activity Originate in the Ventromedial Hypothalamus of the Rat";Annals of the New York Academy of Sciences, 860, pp. 556–559, 1996.
Makoto Bannai, et al.;"Water–Absorbent Polymer as a Carrier for a Discrete Deposit of Antisense Oligodeoxynucleotides in the Central Nervous System"; Brain Research Protocols; 3, 1998, pp. 83–87.
Makoto Bannai, et al.; "Effect of Injection of Antisense Oligodeoxynucleotides of GAD Isozymes into Rat Ventromedial Hypothalamus on Food Intake and Locomotor Activity"; Brain Research, 784, 1998, pp. 305–315.

*Primary Examiner*—William R. A. Jarvis
(74) *Attorney, Agent, or Firm*—Oblon, Spivak, McClelland, Maier & Neustadt, P.C.

(57) ABSTRACT

It is an object of the present invention to treat a patient suffering from symptoms accompanied by non-intentional motions such as poriomania and hyperkinesia, by administering to the patient a substance capable of pre-synaptically or post-synaptically inhibiting the running neurons. In particular, the running neuron-inhibitory substances include a member selected from the group consisting of kainate receptor antagonists, GABA$_B$ receptor agonists, GABA$_A$ receptor agonists, and GABA$_A$ receptor-enhancing substances, or any combination thereof.

8 Claims, 3 Drawing Sheets

METHOD FOR INHIBITING NON-INTENTIONAL BEHAVIOR WITH A RUNNING NEURON INHIBITORY SUBSTANCE

BACKGROUND OF THE INVENTION

The present invention relates to a pharmaceutical composition for treating a symptom accompanied by non-intentional behavior, particularly for treating poriomania or hyperkinesia (including attention-deficit/hyperactive disorder; ADHD) and the use of running neuron inhibitory substance. For some vertebrates such as human, dog or cat, poriomania, especially poriomania and/or hyperkinesia occurring during the night, may cause some problems. Poriomania or hyperkinesia is generally believed to need psychiatric treatments. Particularly, poriomania of elderly person of advanced age was believed to be closely associated with Alzheimer's disease. Such conditions often raise problems, because they not only cause harmful effects to the patients, especially to the patients suffering from other diseases but cause harmful effects to surrounding people. The term "poriomania" herein used means "wandering from home driven by an abnormal impulsus" or "causing an uncontrollable impulsus for wandering or traveling" (see, for example, Stedman's Medical Dictionary, revised $2^{nd}$ edition, 1989, Medical View Publishing Company). The term "hyperkinesia" or "hyperkinetic syndrome" herein used is a general idea including a condition of a disease characterized by having abnormal excess energy and is believed to be a syndrome observed in a little child having a damage in the brain or having mental disability or during epilepsy, including the idea (see the aforementioned Medical Dictionary). Hyperkinesia has been believed to be characterized by excess motions and unstable emotion (see the aforementioned Medical Dictionary). It has been known that such a symptom is also observed for canine. As will be suggested by the foregoing description, the abnormal behaviors of these patients have been considered to be intentional ones.

Thus, antipsychotic drugs, somnifacients or muscle relaxants being capable of suppressing motions of patients have been generally used for treating patients in such conditions. However, these drugs newly cause several troubles, such as obnubilation or systemic muscular relaxation. Moreover, patients have sometimes been physically deprived of their liberty by inevitably binding patients to beds or by placing them in confinement as a symptomatic treatment for the poriomania and hyperkinesia, but the treatment would inflict considerable pain on these patients. In any event, conventionally known therapeutics or drugs has been focusing on preventing patients from freely movement or non-intentional movement, which may damage the quality of life of the patients.

On the other hand, independent of the foregoing clinical investigations, many attempts have been made, during the studies of neuron focused on the running activity, especially on the night running activity. For example, the inventors of the present invention reported that when the ventromedial nucleus of hypothalamus (hereinafter simply referred to as "VMH") of rat was stimulated by water absorbent polymers, the running activity on rat was induced by the pressure stimulus (Yokawa, et. al., Physiology & behavior (1989), 46, 713–717). According to this report, signals from VMH were indicated to be required for the induction of running activity in rat, based on the observation that the running activity did not occur when VMH region had been excised from the animals. Additionally, the inventors demonstrated that the foregoing induction of rat running activity caused by polymers could be inhibited by administration of GABA (γ-aminobutyric acid) (Yokawa, et. al., Physiol. & Behav. (1990), 47, 1261–1264). The inventors also reported that the running activity in rat may be induced by a kind of ionotropic glutamate receptor, kainate receptor agonists (Narita, et. al., Brain Res. (1993), 603, 243–247). According to the report, the running activity in rat was induced by kainate and was not inhibited by GABA but the running activity was inhibited by DNQX(6,7-dinitroquinoxaline-2,3-dione), a kainate receptor antagonist, which suggest that the neuron controlling the running activity in rat may be stimulated through kainate receptors and that $GABA_A$ receptors presynaptically inhibit the neuron controlling the running activity in rat against the kainate receptors. On the other hand, it has been also reported that substances having the competitive inhibitory activity against $GABA_B$ receptors are likewise useful in treatment of neurological disease accompanied by convulsion, Alzheimer's disease or memory retention disorder (Japanese unexamined publication, JP 4-243853).

SUMMARY OF THE INVENTION

The object of the present invention is to provide a pharmaceutical composition which suppresses non-intentional locomotion but do not suppress intentional locomotion. Particularly, the object of the present invention is to provide a pharmaceutical composition for treating diseases including poriomania or hyperkinesia.

The object of the present invention is also to provide a method of treating symptoms accompanied by non-intentional behaviors, comprising the step of administrating the one or more running neuron inhibitory substances or the pharmaceutical composition of the present invention.

The another object of the present invention is to provide the use of running neuron inhibitory substances for producing such pharmaceutical compositions. The inventors have been suggested that there are some neurons in the VMH which were strongly suggested to be involved in the running activity in rat, especially in the night running activity, as previously mentioned. The inventors designated the neuron existing in the VMH region as "running neuron" and concluded that the running neuron is the neuron which regulate the non-intentional locomotion in rat. The hypothalamic region, including the VMH, is believed to be well conserved among vertebrates and the hypothalamic region is phylogenically one of the oldest parts of the central nerve system. Therefore, we propose that the running neuron that we described herein in rats exist also in the VMH region of other vertebrate animals, including humans and canine. Furthermore, it is clinically observed that patients exhibiting poriomania usually give an unreasonable explanation or they say that they forgot the aim of wandering or they had not the intention of wandering. Additionally, hyperkinesia is clinically believed to be an intentional behavior. The inventors took these findings into account and became to believe that the running neuron must exists in other animals than rat such as human and dog, and to associate the input from the neuron with certain behaviors including poriomania and hyperkinesia, from the point of view that poriomania or hyperkinesia in human and certain vertebrates is a "non-intentional behavior" rather than an "intentional behavior" as previously believed. Consequently, the inventors led to invent the pharmaceutical composition and the method, which may inhibit certain behaviors including poriomania and hyperkinesia, but do not inhibit intentional locomotion. Thus, the present invention is a pharmaceutical composition for treating a symptom accompanied by non-intentional behaviors including poriomania and hyperkinesia, which comprises a substance being able to inhibit the running neuron in the presynaptic or postsynaptic manner.

The present invention comprises also the use of a substance being able to inhibit the running neuron in the presynaptic or postsynaptic manner for producing a pharmaceutical composition for treating a symptom accompanied by non-intentional behaviors including poriomania and hyperkinesia.

Particularly, the present invention is a pharmaceutical composition for treating a symptom accompanied by non-intentional behaviors, including poriomania and hyperkinesia. The composition comprises substances selected from the group consisting of $GABA_B$ receptor agonists, $GABA_A$ receptor agonists, or substances that enhance the activity of $GABA_A$ receptor and kainate receptor antagonists, or any combination thereof. The present invention comprises also the use of such substances for producing a pharmaceutical composition for treating a symptom accompanied by non-intentional behaviors including poriomania and hyperkinesia.

DESCRIPTION OF THE PREFERRED EMBODIMENTS

Figure 1:
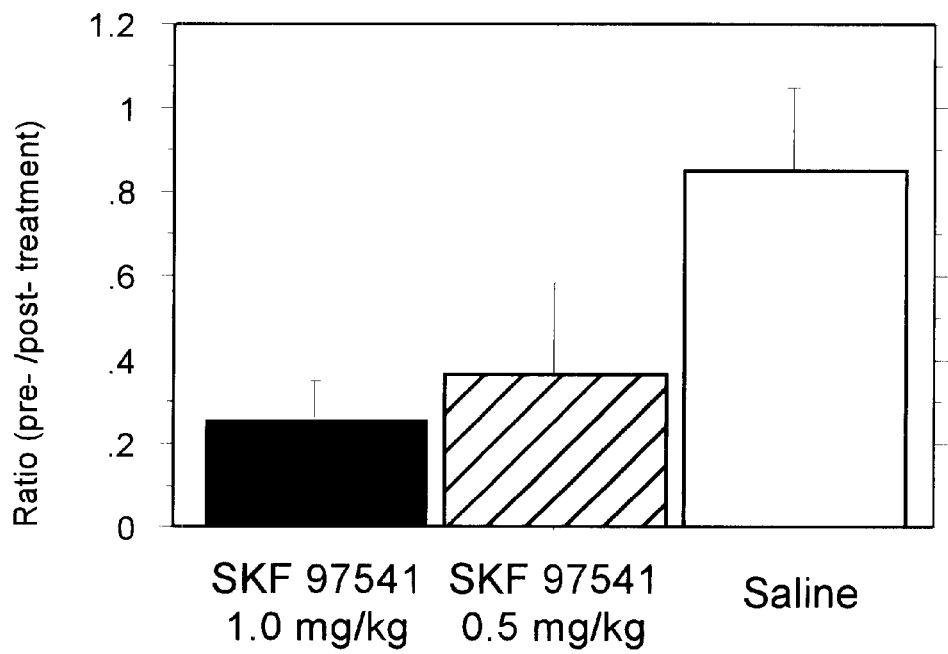
FIG. 1 reveals the comparison of the groups that received intraperitoneal administration of $GABA_B$ receptor agonist SKF67541 with the control group. The axis of ordinate indicates the ratio of running activity before and after the administration.

The pharmaceutical composition having one or more running neuron inhibitory substances and the use of the inhibitory substances for producing the pharmaceutical composition can be commonly applicable to the symptoms accompanied by non-intentional behaviors. They are preferably used for symptoms accompanied by non-intentional systemic locomotion such as poriomania or hyperkinesia. Running neuron inhibitory substances which can be used in the present invention include $GABA_B$ receptor agonists, $GABA_A$ receptor agonists, $GAGA_A$ receptor enhancers (substances which can affect $GABA_A$ receptors and can enhance the activity the receptors), kainate receptor antagonist and any combination thereof. Particularly, $GABA_A$ receptor agonists include, besides GABA, but are not limited to, isoguvacine (1,2,3,6-tetrahydro-4-pyrydinecarboxylic acid), muscimol (5-aminomethyl-3-hydroxyisoxazole), THIP (4,5,6,7-tetrahydroisoxazolo[5,4-c]pyridin-3-ol) and the like. $GABA_B$ receptor agonists include, but are not limited to, baclofen (4-amino-3-(4-chlorophenyl) butanoic acid), SKF97541 (3-aminopropyl (methyl) phosphinic acid) and the like. $GABA_A$ receptor enhancers include, but are not limited to, benzodiazepine and the like, kainate receptor antagonists include, but are not limited to, CNQX (6-cyano-7-nitroquinoxaline-2,3-dione), CNQX disodium salt (6-cyano-7-nitroquinoxaline-2,3-dione disodium)DNQX, GAMS (γ-D-glutamylaminomethylsulphonic acid), NBQX (2,3-dioxo-6-nitro-1,2,3,4-tetrahydrobenzo[f]quinosaline-7-sulphonamide), NBQX disodium (2,3-dioxo-6-nitro-1,2,3, 4-tetrahydorbenzo[f]quinoxaline-7-sulphonamide disodium) and the like.

The pharmaceutical composition of the present invention may be administered orally or parenterally, preferably orally. Parenteral administration includes transcutaneous, ophthalmic administration, administration by inhalation, transnasal and intraperitoneal administration. The dose may be determined depending on the age of the patient, condition of a disease, general condition, body weight, therapeutic pan and desired effects and the like. The pharmaceutical composition of the present invention may be prepared and administered as a dose per day such that the amount of the effective component or the running neuron-inhibitory substance ranges from about 0.1 mg/kg body weight to about 500 mg/kg body weight, preferably about 1 mg/kg body weight to about 100 mg/kg body weight and more preferably about 10 mg/kg body weight to about 50 mg/kg body weight in case of oral administration, and ranges from about 0.001 mg/kg body weight to about 200 mg/kg body weight, preferably about 0.005 mg/kg body weight to about 20 mg/kg body weight and more preferably about 0.05 mg/kg body weight to about 2 mg/kg body weight in case of parenteral administration.

The pharmaceutical composition of the present invention is generally administered to a patient over 1 to 6 times a day and preferably 1 to 3 times a day. The pharmaceutical composition of the present invention may continuously be administered to a patient over a long period of time. If a severe symptom appears at a specific time or during a specific term, however, the pharmaceutical composition may be administered to such a patient over limited times at such a specific time or during such a specific term depending on the intensity of the symptom. In any case, if other therapeutic agents or other therapies are used simultaneously, the dose of the pharmaceutical composition of the present invention is adjusted depending on the amounts and characteristic properties of these agents and therapies. For instance, if the pharmaceutical composition of the present invention is used simultaneous with an anti-psychotic agent, the dose of the former is appropriately reduced depending on the aforementioned factors.

If the pharmaceutical composition of the present invention is administered through the oral route, the composition may be used in the usual dosage forms such as tablets, capsules, powdered drugs, granules, syrup and suspensions. On the other hand, if the composition is administered through the parenteral route, it may be used in such dosage forms as sterilized solutions for injection or for eye drop and aerosols for inhalation.

The pharmaceutical composition of the present invention may further comprise pharmaceutically acceptable excipients. If necessary, the pharmaceutical composition of the present invention may additionally comprise aromatics, colorants, disintegrators, preservatives for stabilization, suspending agents, emulsifying agents and lubricants. In particular, if the pharmaceutical composition of the invention is parenterally administered, the osmotic pressure thereof may be, if necessary, sometimes adjusted. Pharmaceutically and physiologically acceptable substances can be used as the excipients or the additional substances. The specific examples thereof are sugars such as lactose and galactose; starches such as corn starch; fatty acid salts such as magnesium stearate; alginic acid, talc and polyethylene glycol.

The pharmaceutical composition of the present invention comprises the running neuron inhibitory substances as the effective component in an amount ranging from about 1 to 95% by weight and preferably about 10 to about 80% by weight on the basis of the total weight of the composition. The rate of the running neuron inhibitory substances may be chosen depending on factors such as the formulations of the pharmaceutical composition of the present invention, the desired effects to be achieved and the total amount of the pharmaceutical composition to be administered to a patient. In particular, if the pharmaceutical composition of the present invention is orally administered, the composition comprises the running neuron inhibitory substances as the effective component thereof in an amount ranging from 1 to 95% by weight, preferably 10 to 80% by weight, more preferably 20 to 70% by weight and particularly preferably about 20 to about 60% by weight on the basis of the total weight of the pharmaceutical composition. If the pharmaceutical composition of the present invention is administrated by mixing the diet, the composition comprises the running neuron inhibitory substances as the effective component thereof in amount ranging from 0.001 to 10% by weight, preferably 0.01 to 1% by weight on the basis of the total weight of the pharmaceutical composition. On the other hand, if the pharmaceutical composition is parenterally administered, it in general comprises the running neuron inhibitory substances in an amount ranging from about 0.01 to 30% by weight and preferably 0.05 to 20% by weight on the basis of the total weight of the pharmaceutical composition. In any case, if the pharmaceutical composition of the invention comprises a plurality of running neuron inhibitory substances, the amount of the individual running neuron inhibitory substance may be controlled depending on the effect thereof.

The pharmaceutical composition of the present invention can widely be used for treating the mammals, including human, suffering from psychosis accompanied by unintentional behaviors such as poriomania and hyperkinesia, such as human, canine, feline or domestic animals such as bovine and porcine, with such symptoms. In addition, the running neuron-inhibitory substances may be used for the preparation of such a pharmaceutical composition for controlling unintentional behaviors such as poriomania and hyperkinesia, observed in mammals including human.

EXAMPLES

Example 1

Effect of $GABA_B$ Receptor Agonist, SKF97541, on Intentional Behaviors

Rats (Wistar-Imamichi; 7-week-old) were kept in a cage equipped with a running wheel. The animals were kept under such lighting conditions that the lighting was initiated at 7:00 and it was stopped at 19:00, while the animals were allowed to freely eat diet and drink water. They were kept over 3 weeks without subjecting them to any treatment or they were not subjected to any treatment until they sufficiently habituated to the keeping environment or the cage. At this stage, the quantity of the running activity thereof in the night was found to be almost constant.

These animals were treated by intraperitoneal administration of $GABA_B$ receptor agonist, SKF97541, in an amount of 1.0 mg/kg or 0.5 mg/kg at around 18:00. A group of these animals to which physiological saline had separately been administered was used as a control group. Regarding the quantity of running, the counts detected by a sensor equipped with a running wheel were inputted to a computer at intervals of 30 minutes to thus evaluate the accumulated counts in the night, which was defined to be the quantity of acts in the night. Thus, the relative rate of the accumulated count observed for the individual animal was calculated while the accumulated count observed for each animal prior to the treatment was assumed to be 1.

The results thus obtained are shown in FIG. 1. As will be seen from the data shown in FIG. 1, an inhibitory effect on the order of about 40 to 60%, relative to that observed for the control group, can be achieved even in the group to which 0.5 mg/kg of SKF97541 was administered. The inhibitory effect is estimated to be about 70% for the group to which 1.0 mg/kg of SKF97541 was administered. The foregoing clearly indicates that the $GABA_B$ receptor agonist shows a considerable effect on the quantity of rat's running activity in the night and the effect is dependent upon the dose of the antagonist.

Example 2

Effect of $GABA_B$ Receptor Agonist, SKF97541, on Unintentional Behaviors

A $GABA_B$ receptor agonist, SKF97541, was intraperitoneally administered to rats, which had been kept under the same conditions used in Example 1, in an amount of 0.5 mg/kg and these animals were put in water maintained at a temperature ranging from 35 to 37° C. after 30 minutes to 3 hours from the administration of the antagonist. The container (or pool) for the water used herein had a depth of 55 cm, a height from the surface of the water to the upper edge of the container of 30 cm and a cross sectional area of 1200 $cm^2$. The rats were forced to swim in the pool to determine the number of strokes by the forelimbs of these animals per 5 minutes. A group of these animals to which physiological saline had separately been administered was used as a control group.

Figure 2:
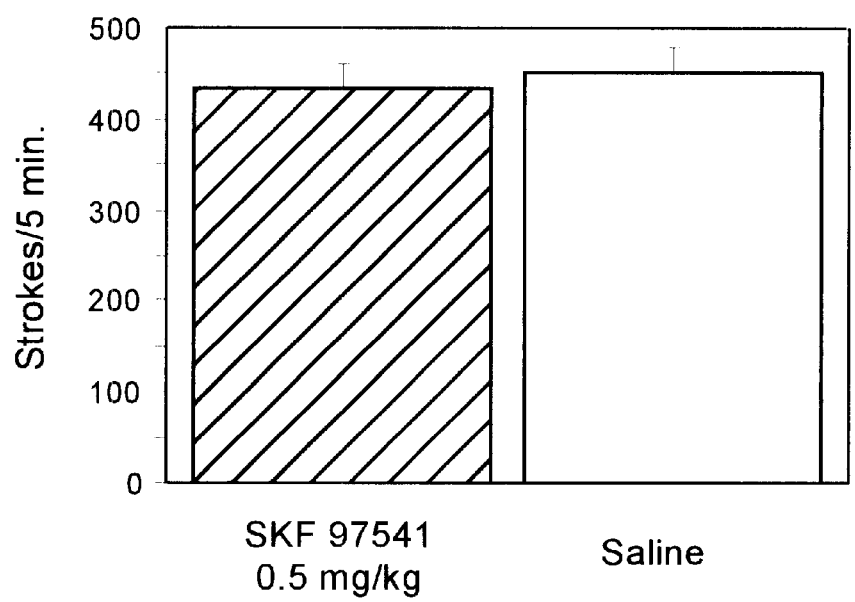
FIG. 2 reveals the result of forced swimming test for the $GABA_B$ receptor agonist administrated group and the control group. The axis of ordinate indicates the frequency of webbing of rats by their fore paws per 5 minutes.

As a result, it was demonstrated that the number of strokes as the intentional motions is not reduced by the administration of the $GABA_B$ receptor agonist (see FIG. 2). This clearly indicates that the $GABA_B$ receptor agonist does not affect the intentional motions to any significant extent.

Example 3

Analysis of Effect of Running Neurons on Unintentional Behaviors

Using rats, which had been kept under the same conditions used in Example 1, the ventromedial nucleus of hypothalamus (VMH) on both sides thereof were lesioned and the quantity of running motions of these animals were determined. A conductive wire of tungsten coated with Teflon was passed through a glass tube (inner diameter: 0.6 mm; outer diameter: 1.0 mm) and the upper end of the glass tube was sealed with an adhesive (Alon Alpha) to thus fix the conductive wire to the glass tube. On the other hand, the conductive wire was pulled out of the lower end of the glass tube in a length of 0.5 mm, followed by peeling off the coated layer from that portion of the wire and fixing or sealing the lower end of the glass tube with putty. The resulting assembly was used as an electrode for breakage. The VMH's on both sides of each animal were lesioned by applying anesthesia to the animal, kept under the foregoing conditions, using pentobarbital, fixing the animal and the electrode to a brain localization and fixing device and the lesion of the VMH's on both sides according to the brain map of Paxinos & Watson.

A DC current of 5 mA was applied to the device through an isolator for 10 seconds. At this stage, the minus pole of the isolator was connected to the electrode, while the plus pole thereof was connected to the forelimb of a rat. Moreover, a control group was treated by inserting the electrode into the VMH of the animal, then allowing the electrode to stand for 60 seconds without applying any electric current thereto and subsequently removing the electrode. The running activity of each animal per day was determined using the rats whose VMH's were electrically lesioned. The date on which the lesion was carried out was defined to be 0th day (day 0).

Figure 3:
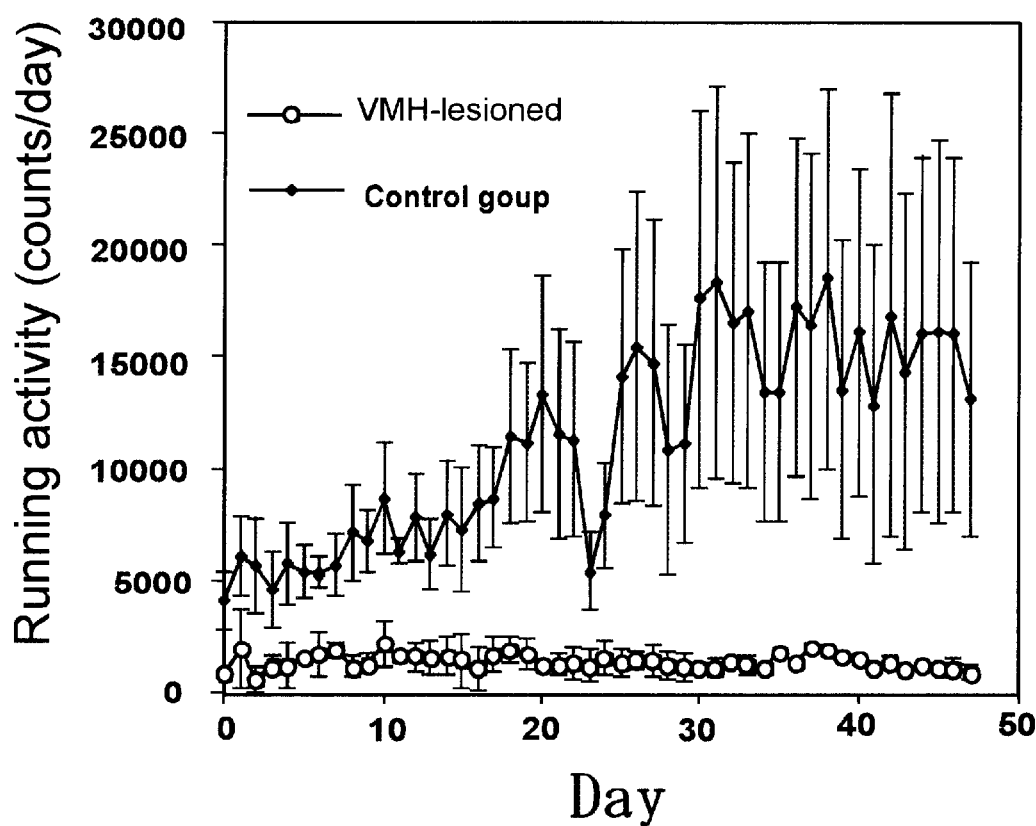
FIG. 3 reveals the result of running activity for the ventromedial nucleus of hypothalamus lesioned group and the control group.

Regarding the running activity of each animal, the counts detected by a sensor equipped with a running wheel were inputted to a computer at intervals of 30 minutes to thus evaluate the accumulated counts over 24 hours, which was defined to be the quantity of acts in the night. Thus, the relative rate of the accumulated count observed for the individual animal was calculated while the accumulated count observed for each animal prior to the treatment was assumed to be 1. As a result, it was found that the running activity, per day, observed for the group whose VMH's had been lesioned is reduced to a considerably low level as compared with that observed for the control group (see FIG. 3).

Example 4

Analysis of Effect of Running Neurons on Intentional Behaviors

Figure 4:
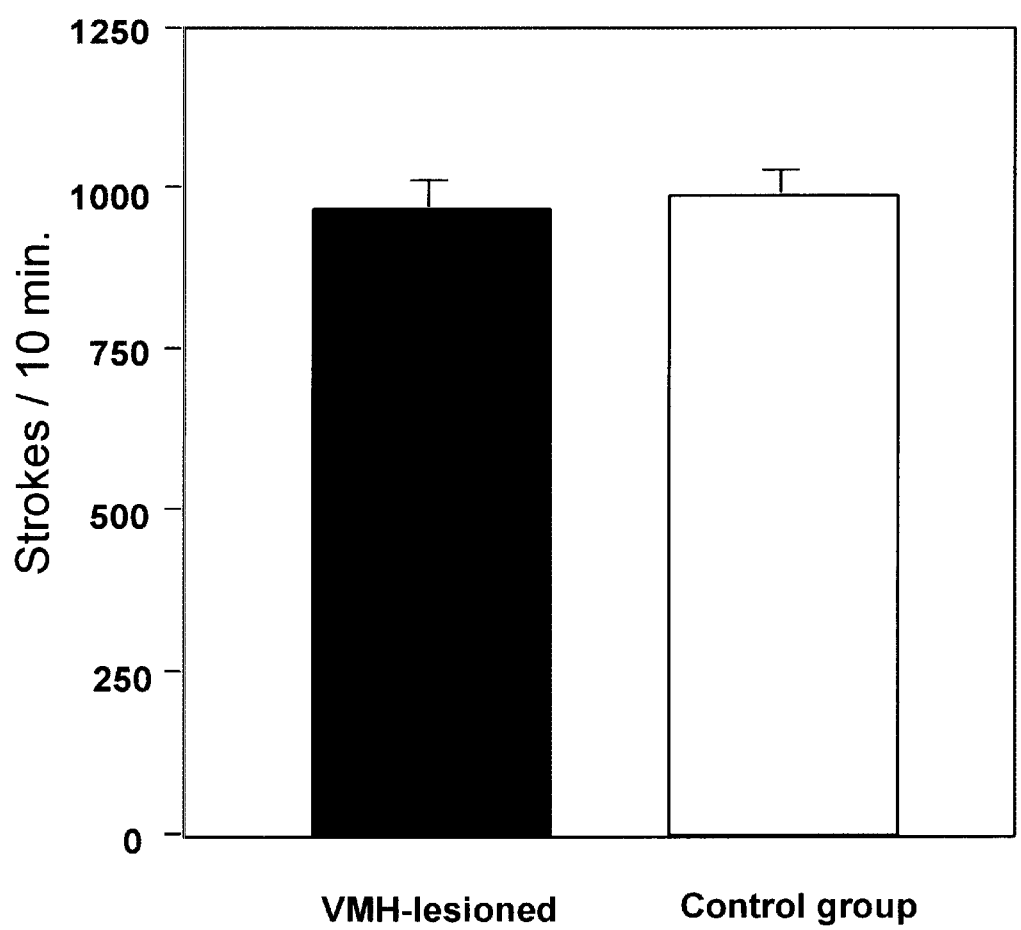
FIG. 4 reveals the result of forced swimming test for the ventromedial nucleus of hypothalamus lesioned group and the control group. The axis of ordinate indicates the number of strokes of rats by their forelimbs per 10 minutes.

Forced swimming experiments were conducted using rats whose VMH's had electrically been lesioned by the same method used in Example 3. In this respect, the forced swimming experiments were conducted by repeating the same procedures used in Example 2. The control group was established by the same method used in Example 3. As a result, it was confirmed that the number of strokes by the forelimbs of each rat, whose VMH's had electrically been broken, in the water was approximately identical to that observed for the control group (see FIG. 4). This clearly indicates that any intentional motions are never inhibited in the group whose VMH's had electrically been lesioned or whose running neurons had been lesioned.

Example 5

A male Pomeranian of 11 years old was used. The dog was established to have been demented and to have suffered from poriomania. About 200 g of a canned feed for dogs (Maintenance Canned Beef available from Nippon Hills Colgate Company) per day was fed to this animal in two portions in the morning and evening. On the other hand, water was available ad libitum.

The experiment was conducted in the laboratory under controlled conditions of room temperature of about 22° C. The cage (150 cm×90 cm) was illuminated by infrared light and the activity of the experimental animal in the night was detected by a monochrome CCD camera. The traces of activity were recorded on a microcomputer every 10 minutes. The traces were recorded for 2 days before treatment, after the animal was maintained and acclimatized to the conditions, and the records were used as the pre-treatment data. The data recording started at about 18:00 and the activity was recorded for 800 minutes. At 18:00 on the treatment date, the animal was fed by the dog food containing 150 mg of powdered GABA and its activity in the night was recorded as post-treatment data. The results were shown in Table 1.

TABLE 1

| | migration length (cm) | migration time (minutes) | number of episodes | mean duration time of each episode (minutes) |
|---|---|---|---|---|
| pre-treatment | 1848 | 24.15 | 8 | 4 |
| post-treatment | 44.7 | 1.4 | 2 | 0.7 |

The migration time is the time of the migration of the animal during the experiment. The migration length is the distance of migration of the animal during the experiment. The start of poriomaniac behavior was defined as the start of migration came after the quiescent state of not less than 10 minutes and the end of the poriomaniac behavior was defined as the stop of migration which was confirmed to be maintained for less than 10 minutes. One incident of the poriomaniac behavior was defined as the behavior from the start to the end of the aforementioned migration. One episode means one incident of the poriomaniac behavior. The number of episodes and the mean duration time of episodes are shown in Table 1. The experimental dog showed the significant decrease in each parameter compared to pre-treatment data, when the animal was administrated by 150 mg of GABA. General symptoms were examined in the similar experiment, but no particular notable events were observed. This suggests that GABA specifically affected the poriomaniac behavior. These data indicates the possibility of treating poriomania and hyperkinesia by administrating the running neuron inhibitors such as GABA agonists and kainate receptor agonists.

The use of the pharmaceutical composition according to the present invention would permit the inhibition of unintentional motions such as poriomania and hyperkinesia without any inhibition of intentional motions. Moreover, a therapeutic agent for inhibiting unintentional motions such as poriomania and hyperkinesia can be prepared by the method of using running neuron-inhibitory substances according to the present invention.

What is claimed:

1. A method of treating symptoms accompanied by non-intentional behaviors, comprising the step of administrating one or more running neuron inhibitory substances.

2. The method of claim 1, wherein the non-intentional behavior is selected from the group consisting of poriomania and hyperkinesia.

3. The method of claim 1, wherein the running neuron inhibitory substance is selected from the group consisting of kainate receptor antagonists, $GABA_B$ receptor agonists, $GABA_A$ receptor agonists, $GABA_A$ receptor enhancers and a combination thereof.

4. The method of claim 3, wherein the running neuron inhibitory substance is a $GABA_A$ receptor agonist.

5. The method of claim 3, wherein the running neuron inhibitory substance is a $GABA_B$ receptor agonist.

6. The method of claim 4, wherein $GABA_A$ receptor agonist is selected from the group consisting of isoguvacine, muscimol and THIP.

7. The method of claim 5, wherein $GABA_B$ receptor agonist is selected from the group consisting of baclofen and SKF97541.

8. The method of claim 3, wherein $GABA_A$ receptor enhancer is benzodiazepine.

* * * * *